(12) United States Patent
Druke et al.

(10) Patent No.: US 7,756,036 B2
(45) Date of Patent: Jul. 13, 2010

(54) SYNCHRONOUS DATA COMMUNICATION

(75) Inventors: Michael B. Druke, Half Moon Bay, CA (US); Christopher J. Jacques, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 173 days.

(21) Appl. No.: 11/479,160

(22) Filed: Jun. 30, 2006

(65) Prior Publication Data

US 2007/0147250 A1 Jun. 28, 2007

Related U.S. Application Data

(60) Provisional application No. 60/753,991, filed on Dec. 22, 2005.

(51) Int. Cl.
G01R 31/08 (2006.01)
(52) U.S. Cl. ...................................... 370/235
(58) Field of Classification Search ................. 370/235, 370/238.1
See application file for complete search history.

(56) References Cited

U.S. PATENT DOCUMENTS

| | | |
|---|---|---|
| 5,068,851 A | 11/1991 | Bruckert et al. |
| 5,652,711 A | 7/1997 | Vennekens |
| 5,762,458 A | 6/1998 | Wang et al. |
| 6,021,129 A | 2/2000 | Martin et al. |
| 6,035,228 A | 3/2000 | Yanof et al. |
| 6,182,120 B1 | 1/2001 | Beaulieu et al. |
| 6,198,971 B1 | 3/2001 | Leysieffer |
| 6,424,625 B1 * | 7/2002 | Larsson et al. ............... 370/236 |
| 6,674,731 B1 | 1/2004 | Bradshaw et al. |
| 6,728,599 B2 * | 4/2004 | Wang et al. .................. 700/258 |
| 6,760,337 B1 | 7/2004 | Snyder, II et al. |
| 6,920,586 B1 | 7/2005 | Moyer |
| 7,440,793 B2 | 10/2008 | Chauhan et al. |
| 2002/0080719 A1 * | 6/2002 | Parkvall et al. .............. 370/235 |
| 2002/0181503 A1 * | 12/2002 | Montgomery, Jr. .......... 370/468 |
| 2003/0112758 A1 * | 6/2003 | Pang et al. ................... 370/235 |
| 2004/0008693 A1 * | 1/2004 | Grove et al. ........... 370/395.52 |
| 2004/0125825 A1 * | 7/2004 | Lym et al. .................... 370/519 |
| 2004/0196861 A1 | 10/2004 | Rinchiuso et al. |
| 2005/0058134 A1 * | 3/2005 | Levi et al. .................... 370/389 |
| 2005/0132104 A1 * | 6/2005 | Brown ......................... 710/36 |
| 2005/0154493 A1 | 7/2005 | Wang et al. |
| 2005/0199728 A1 * | 9/2005 | Schmidt et al. ........ 235/462.46 |
| 2005/0265341 A1 * | 12/2005 | Benedyk et al. ............. 370/389 |

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner*—Kwang B Yao
*Assistant Examiner*—Tung Q Tran

(57) ABSTRACT

Methods, apparatus, and computer program products that synchronously communicate data packets between a first node and a second node. Data packets are transmitted from the first node without waiting for acknowledgment of receipt by the second node. Acknowledgment of receipt of a given data packet is subsequently received at the first node. The acknowledgement is received substantially at a predetermined time following transmission of the given data packet. The acknowledgement indicates that the second node received the given data packet uncorrupted.

32 Claims, 5 Drawing Sheets

U.S. PATENT DOCUMENTS

| | | | |
|---|---|---|---|
| 2007/0147385 A1 | 6/2007 | Druke et al. | |
| 2007/0150631 A1 | 6/2007 | Druke et al. | |
| 2007/0153811 A1* | 7/2007 | Venters et al. | 370/395.62 |
| 2008/0022165 A1 | 1/2008 | McKim et al. | |
| 2008/0159126 A1* | 7/2008 | Takagi et al. | 370/222 |
| 2009/0012532 A1 | 1/2009 | Quaid et al. | |
| 2009/0046735 A1 | 2/2009 | Regnier et al. | |

OTHER PUBLICATIONS

U.S. Appl. No. 11/480,282 Final Office Action, mailed Jan. 7, 2009, 19 pages.

11-479203 Non-Final Office Action mailed Oct. 2, 2008, 16 pages.

11-480282 Non-Final Office Action mailed Jun. 23, 2008, 12 pages.

PCT/US06/62366 International Search Report mailed Oct. 1, 2008, 5 pages.

PCT/US06/62366 Written Opinion of the International Search Authority dated Sep. 3, 2008, 7 pages.

PCT/US06/62367 International Search Report mailed Jul. 1, 2008, 2 pages.

PCT/US06/62367 Written Opinion of the International Search Authority mailed Jul. 1, 2008, 8 pages.

PCT/US06/62372 International Search Report mailed May 8, 2008, 2 pages.

PCT/US06/62372 Written Opinion of the International Search Authority mailed May 8, 2008, 7 pages.

U.S. Appl. No. 11/479,203 Final Office Action mailed Apr. 14, 2009, 20 pages.

U.S. Appl. No. 11/480,282 Non-Final Office Action mailed May 26, 2009, 17 pages.

U.S. Appl. No. 11/479,203 Non-Final Office Action mailed Sep. 18, 2009, 23 pages.

* cited by examiner

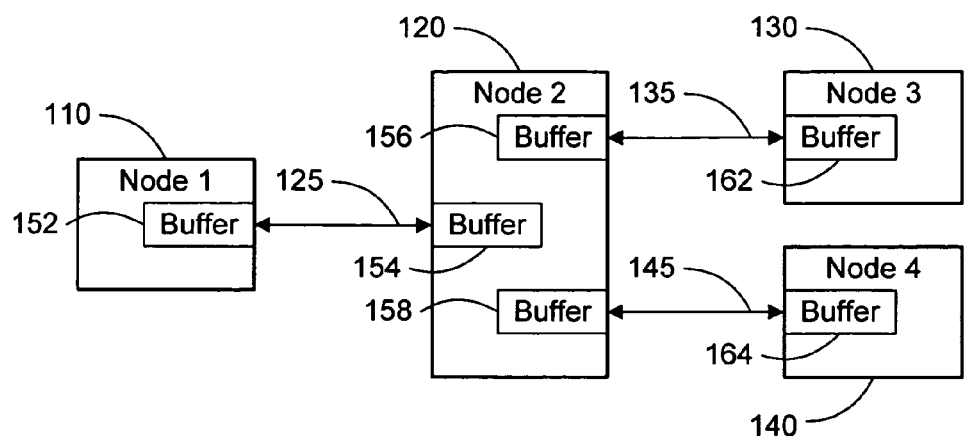
FIG._1
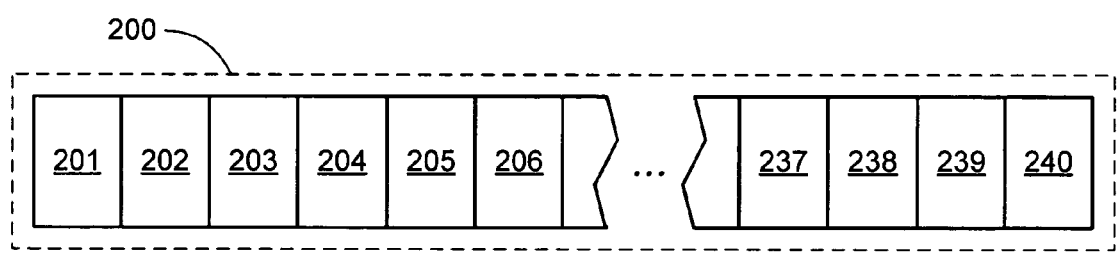
FIG._2

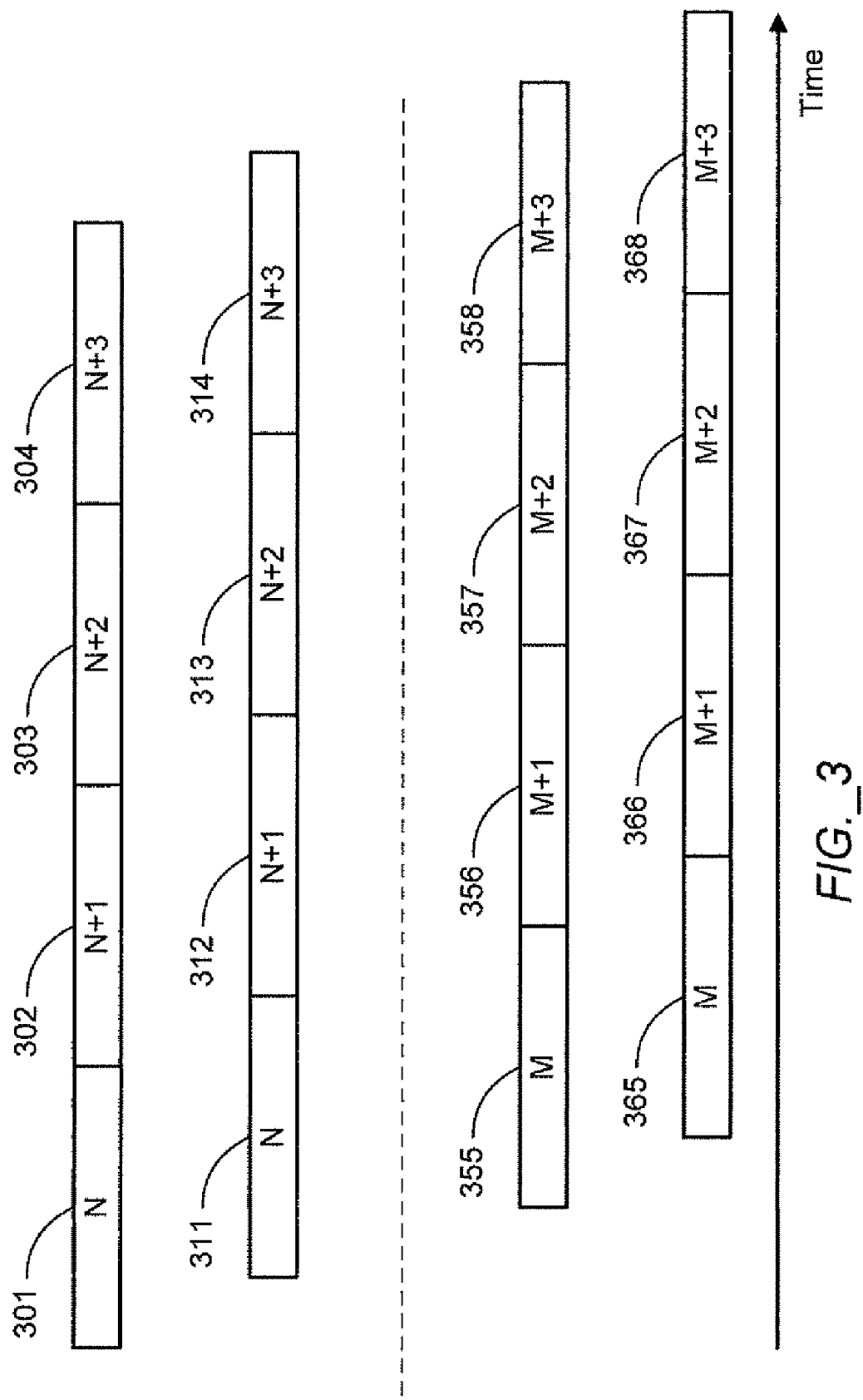

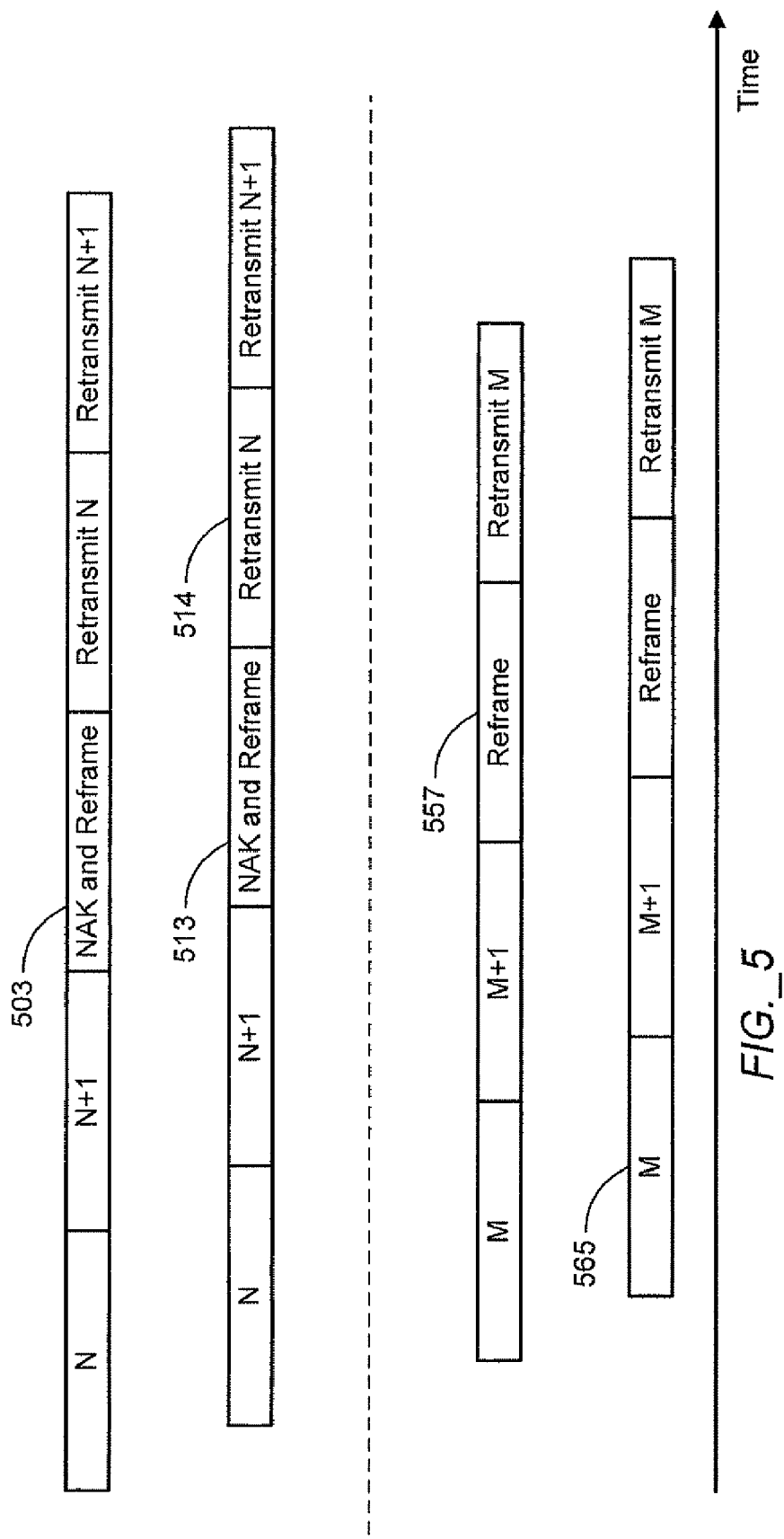
FIG._5

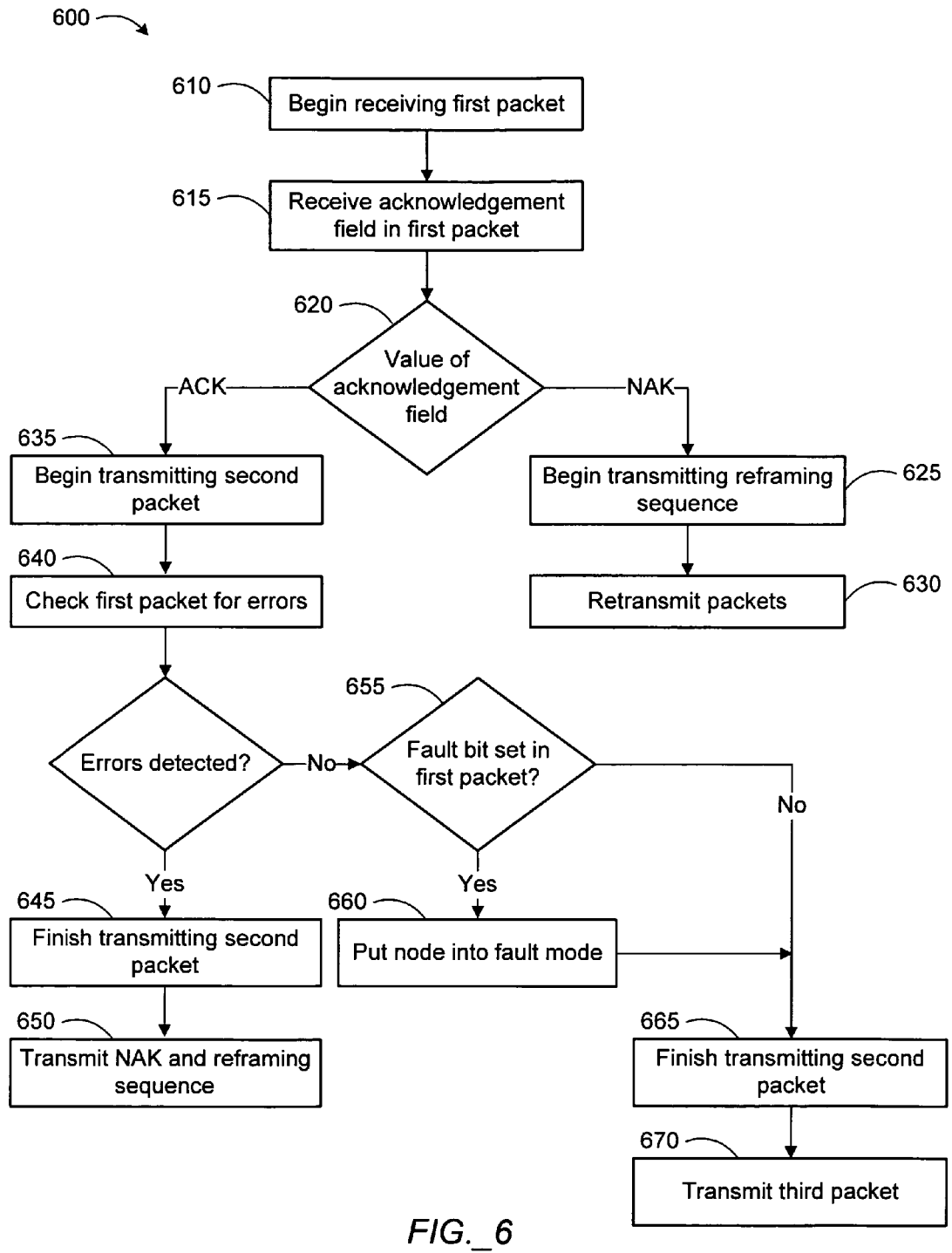
FIG._6

SYNCHRONOUS DATA COMMUNICATION

CLAIM OF PRIORITY

This application claims the benefit of U.S. Provisional Patent Application Ser. No. 60/753,991, filed on Dec. 22, 2005, the entire contents of which are hereby incorporated by reference.

BACKGROUND

The present disclosure relates to information systems.

Certain applications have high bandwidth requirements and strict synchronization, latency, and reliability requirements for communications. Robot-assisted surgery, for example, requires a high bandwidth to transmit control and feedback signals in real time. The synchronization and latency requirements of such applications are strict, because ideally there should be as little lag as possible between the movements of a surgeon and the movements of the robot. In these applications the communications must be highly reliable, because a data transmission error could injure a patient.

One conventional communication system used in robot-assisted surgery uses several hundred paths (e.g., wires) to connect a surgeon's control console to robotic arms. The use of hundreds of paths, however, makes setup and maintenance of the system cumbersome and requires substantial room to route all of the paths.

Conventional communication standards provide acceptable performance in some areas but are lacking in others. The IEEE-1394 interface standard, for example, provides synchronous, serial, point-to-point communication. IEEE-1394 channels have a guaranteed bandwidth but only can provide synchronization to within approximately 125 microseconds. Such performance may not be sufficient for certain applications requiring tighter synchronization.

SUMMARY

In one aspect, a method and computer program product are provided that include transmitting a first data packet from a first node to a second node. The first data packet includes a data field, which includes non-filler data from the first node. A second data packet is transmitted from the first node to the second node after the transmission of the first data packet. The transmission of the second data packet begins before any acknowledgement information corresponding to the first data packet has been received from the second node. A third data packet that was transmitted from the second node is received at the first node. The third data packet includes acknowledgement information indicating whether the first data packet was received correctly by the second node. The transmission of the first data packet and the receipt of the third data packet are interlocked such that the third data packet is received substantially a predetermined amount of time after the transmission of the first data packet.

Particular implementations may include one or more of the following features. The second data packet can be transmitted regardless of whether the first node has any non-filler data to place in a data field of the second data packet. The first, second, and third data packets can each include respective flow-control information. The flow-control information in the first and second data packets relates to the first node, and the flow-control information in the third data packet relates to the second node. The flow-control information can include separate flow-control information for multiple channels. The first data packet can include header information indicating which of a plurality of channels the non-filler data is being transmitted on. The first and second data packets can each include an indication of a fault status of the first node. The third data packet can includes an indication of a fault status of the second node. The first, second, and third data packets can have a same length.

A fourth data packet can be received at the first node. The fourth data packet is transmitted from the second node and includes acknowledgement information indicating whether the second data packet was received correctly by the second node. The transmission of the second data packet and the receipt of the fourth data packet can be interlocked such that the fourth data packet is received substantially the predetermined amount of time after the transmission of the second data packet. A fifth data packet can be received at the first node before the third data packet is received. The fifth data packet is transmitted from the second node before the third data packet, and the fifth data packet does not include acknowledgement information indicating whether a particular data packet was received correctly by the second node.

In another aspect, a method and computer program product are provided that include synchronously communicating data packets between a first node and a second node. Data packets are transmitted from the first node without waiting for acknowledgment of receipt by the second node. Acknowledgment from the second node of receipt of a given data packet is subsequently received at the first node. The acknowledgement is received substantially at a predetermined time following transmission of the given data packet indicates that the second node received the given data packet uncorrupted. In a particular implementation, a specific data packet can be resent if acknowledgement of receipt of the specific data packet is not received substantially at the predetermined time following transmission of the specific data packet.

In yet another aspect, a method is provided that includes transmitting a first data packet from a first node to a second node. The first data packet includes a first data field that includes non-filler data from the first node. The first data packet is received at the second node, and the receipt of the first packet takes a finite amount of time. The transmission of a second data packet from the second node to the first node is begun after the receipt of the first data packet has begun, but before the receipt of the first data packet has finished. The second data packet is received at the first node, and the receipt of the second data packet takes a finite amount of time. The transmission of a third data packet from the first node to the second node is begun after the transmission of the first data packet has finished, after the receipt of the second data packet has begun, and before the receipt of the second data packet has finished. The transmission of the third data packet begins before any acknowledgement information corresponding to the first data packet has been received from the second node. The third data packet is received at the second node, and the receipt of the third data packet takes a finite amount of time. The transmission of a fourth data packet from the second node to the first node is begun after the transmission of the second data packet has finished, after the receipt of the third data packet has begun, and before the receipt of the third data packet has finished. The transmission of the fourth data packet begins before any acknowledgement information corresponding to the second data packet has been received from the first node. The fourth data packet includes acknowledgement information indicating whether the first data packet was received correctly by the second node. The transmission of the first data packet and the transmission of the fourth data packet are interlocked such that the fourth data packet is transmitted substantially a predetermined amount of time after the transmission of the first data packet. The fourth packet is received at the first node, and the acknowledgement information indicating whether the first data packet was received correctly is processes at the first node. The first node retransmits the first data packet if the first data packet was not received correctly at the second node.

Particular embodiments can be implemented to realize one or more of the following advantages. A transmitter and a receiver can be synchronized very precisely (e.g., to within substantially 10 microseconds or less). Latency can be bounded and kept low (e.g., less than substantially 10 microseconds). Data can be transmitted with low latency over a single physical path connector. A same communication protocol can be used for multiple communication links operating at different speeds in a single system. The communication protocol can be implemented inexpensively in hardware. Bandwidth can be used for data transmission that otherwise would be used waiting for an acknowledgement. Error detection and recovery can be performed on flow control information and acknowledgement information at the same time. Fault information can be transmitted throughout a system rapidly. Multiple independent streams of data at different priority levels can be transmitted throughout the system.

These general and specific aspects may be implemented using a method, an apparatus, a system, or any combination of methods, apparatus, and systems.

The details of one or more embodiments of the invention are set forth in the accompanying drawings and the description below. Other features, aspects, and advantages of the invention will become apparent from the description, the drawings, and the claims.

BRIEF DESCRIPTION OF THE DRAWINGS

FIG. 1 is a block diagram of a system that includes multiple nodes connected by links.

FIG. 2 is a diagram of the structure of a data packet.

FIG. 3 is a timing diagram of packet transmission between nodes.

FIG. 5 is a timing diagram of an error recovery scenario.

FIG. 6 is a flowchart of a process performed at a node.

Like reference numbers and designations in the various drawings indicate like elements.

DETAILED DESCRIPTION

Figure 4:
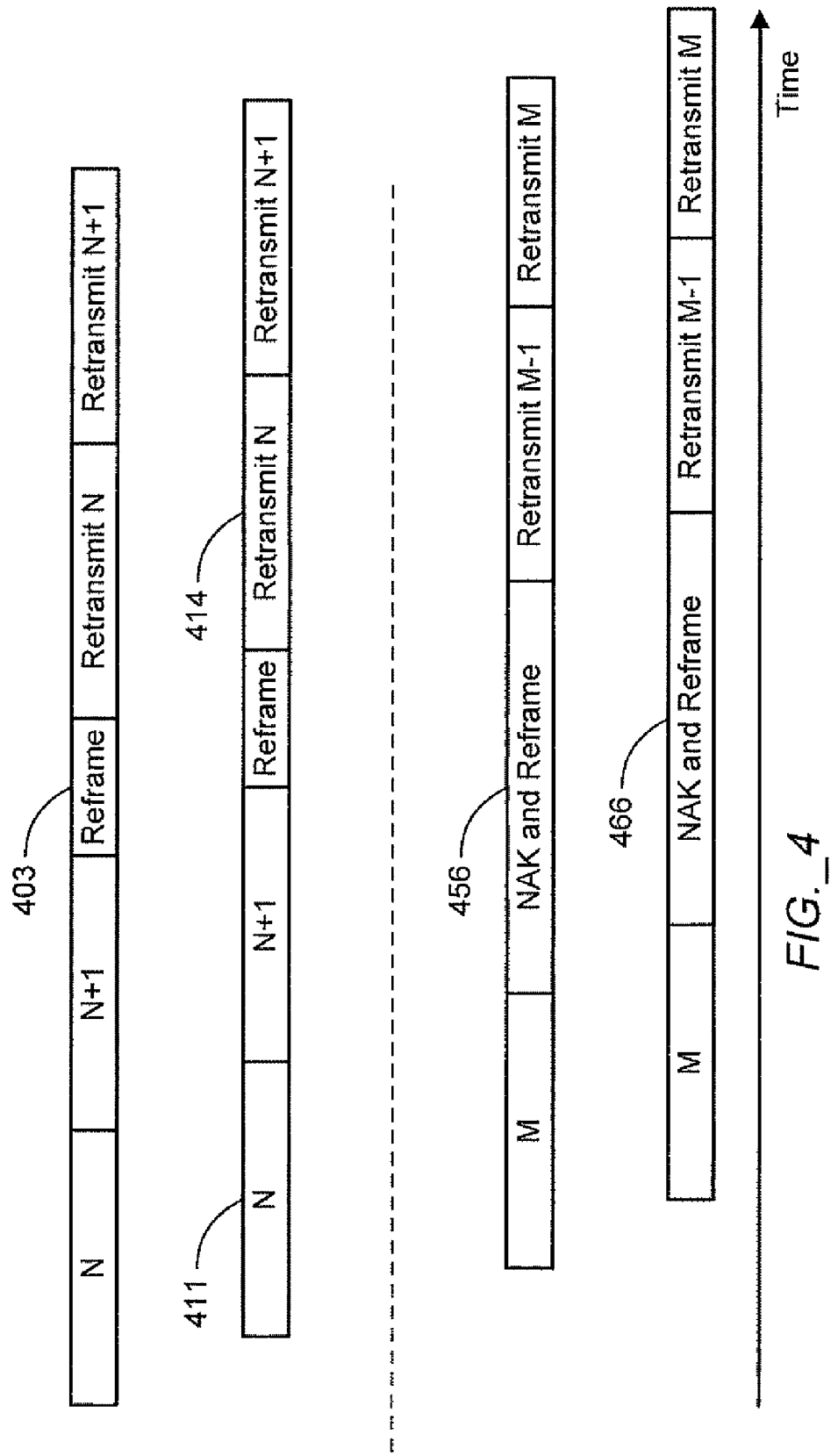
FIG. 4 is a timing diagram of an error recovery scenario.

A link layer is described that uses a substantially continuous stream of full-duplex serial data between two system nodes. Nodes can include, for example, computers, programmable processors, field-programmable gate arrays (FPGAs), or other data processing apparatus. The data is divided into fixed-length packets. Each fixed-length packet can contain data, error-checking information, flow control information, diagnostic information, fault information, and retransmission control information. The data in each packet can include hardware-level data or portions of messages (e.g., software messages).

The fixed-length packets are continuously transmitted between two nodes, regardless of whether data is available to transmit. When no data is available to transmit, the data field of a packet can be filled with "filler" data that can be discarded at the receiving node. The transmitted packets include acknowledgements of previously received packets, and a transmitting node will transmit a first packet and begin transmitting at least one subsequent packet before receiving an acknowledgement of the first packet from the receiving node. The transmission and receipt of packets at a node are interlocked, as will be described in more detail below.

As shown in FIG. 1, data from a first node 110 can be transmitted to multiple destination nodes—for example, a second node 120, a third node 130, and a fourth node 140—by multiplexing the data on a link. Nodes between the first node 110 and a particular destination node can route the data. The first node 110 can transmit data for the second node 120 over a first link 125. The first node 110 also can transmit data for the third node 130 over the first link 125 to the second node 120, and the second node 120 can route the data to the third node 130 over a second link 135. Likewise, the first node 110 can transmit data for the fourth node 140 over the first link 125, and the second node 120 can route the data to the fourth node 140 over a third link 145.

The designation of a destination node can be handled, in one implementation, in a message that is included in the data being transmitted. In this implementation, the second node 120 typically processes at least part of a message being sent from the first node 110 before sending packets containing portions of the message to the destination node. If the second node 120 is itself the destination node, the message need not be transmitted any further.

In some systems, communications occur more frequently between the first node 110 and the third node 130 and the fourth node 140 than communications between the third node 130 and the fourth node 140 occur. In such systems, the first link 125 can be a higher-speed link than the second link 135 or the third link 145 to provide sufficient capacity for the greater volume of data that passes over the first link 125.

The nodes 110, 120, 130, and 140 can include one or more hardware data buffers 152-164 that receive messages and hold the messages until software executing on the respective node or on a data processing apparatus in communication with the respective node is ready to receive the messages.

As shown in FIG. 2, a fixed-length packet 200 of one implementation can include multiple bytes 201-240. While a 40-byte packet is shown, the fixed-length packet can be other lengths. In the implementation shown, control information is placed in 8 of the 40 bytes, and data is placed in the remaining 32 bytes. The first byte 201 is a synchronization field that can be used to maintain byte framing at a node that receives the packets. An additional synchronization byte can periodically be added to a packet (e.g., once every 128 packets) to compensate for clock drift between nodes. The second byte 202 is an acknowledgement field that indicates whether the last packet received by the node transmitting packet 200 was received correctly (e.g., included valid error-checking information). The second byte 202 can be set to one value (e.g., 0xAC) to indicate an acknowledgement (ACK) that the last packet was received correctly and to the inverse value (e.g., 0x53) to indicate that the last packet was not received correctly (no acknowledgement, or NAK). In one implementation, any value other than the acknowledgement value can be interpreted as no acknowledgement. In this implementation, if the NAK value is the inverse of the ACK value, an 8-bit error is required to transform a transmitted NAK into an ACK.

The third byte 203 is a response field that contains multiple control bits, such as a test-mode bit that indicates the system is in a diagnostic test mode and an XOFF bit for each of multiple message channels (e.g., low-, medium-, and high-priority channels). The control bits can also include a retransmission bit that when set indicates that the packet 200 is a retransmission of an earlier packet. One or more of the control bits also can be fault bits, which indicate that an error has occurred in the system.

The fourth byte 204 is a header field. The header field can include multiple subfields, such as a channel-select subfield and a command subfield. The channel-select subfield is used to indicate on which priority channel the data in the packet 200 is being transmitted. The command subfield can include instructions to flush buffers and restart a message stream. The command subfield can include instructions requesting that particular data be sent over the hardware channel or codes to identify such data. The command subfield also can be used to synchronize the system. For example, at the beginning of a synchronization cycle, a packet that contains the synchronization command can be sent, enabling subsystems within the system maintain synchronization (e.g., to within 10 microseconds). The fifth byte 205 is a sequence number field that contains a sequence number that can be used by a receiving node to detect transmission errors. The sixth byte 206 through the $37^{th}$ byte 237 belong to a data field that holds 32 bytes of data, such as a message or portion of a message.

The $38^{th}$ byte 238 is an end-of-packet field that can specify how many of the bytes in the data field correspond to a message and how many bytes are filler bytes. The end-of-packet field also can include an end-of-message indicator bit that is set when the bytes in the data field end a message. The end-of-message indicator bit can trigger an interrupt at the receiving node. The $39^{th}$ byte 239 and $40^{th}$ byte 240 are part of an error-checking field that can contain, in one implementation, a 16-bit CRC value (e.g., computed using the CCITT 16-bit CRC algorithm). When a node receives a packet, the node can use the error-checking field to determine whether an error occurred while the packet was being transmitted or received.

The structure of the packet 200 allows fault reaction logic (FRL) signals that indicate a fault in a node to be communicated in multiple ways. For example, FRL signals can be transmitted in packet control information (e.g., in the control bits of the response field of packet 200), and/or in messages. Transmitting FRL signals directly in packet control information allows fault information to be transmitted very quickly system wide and to be handled at a very low level. A system-wide fault signal can be propagated without software intervention, and fault reaction hardware can put the system in a safe state when a fault signal is received. Once the problem that caused the fault has been solved (e.g., by the intervention of a human operator), the fault signal can be cleared and the system can return to an operational state. When the fault signal is cleared, the FRL signal indicating a fault typically is not transmitted in the packet control information until another fault occurs.

An example of a system in which the quick propagation of a fault signal is beneficial is a robotic surgery system. Such a system can include multiple robotic arms that hold surgical instruments or devices (e.g., laparoscopes, endoscopes, lights, cameras, and insufflators), some of which may be inside a patient. The robotic arms typically are manipulated remotely by a surgeon. Communications between controls that the surgeon operates and the nodes that control the robotic arms can use the methods, systems, and apparatus described in the current disclosure. If a fault occurs in such a system, the robotic arms can be locked in place so that the patient is not injured by unintended movements of the robotic arms. When the system fault occurs and a system fault is propagated between nodes, brakes can be applied to the joints of the robotic arms and communication of movement commands can be suspended until the fault is cleared by a human operator or automatically by a system monitoring unit.

The described packet structure allows data such as messages to be sent on a single channel or on multiple channels that are multiplexed on a serial connection. The channel on which a particular message is being sent is indicated by the channel select subfield in the packet 200. The system software can place messages in different hardware buffers for each channel (e.g., using different addresses), and the system hardware automatically assigns a message to a channel based on which buffer the message was placed into. The multiple channels can be assigned different priority levels. In one implementation, when messages of differing priorities are waiting to be transmitted, a packet or group of packets containing data being transmitted on a high-priority channel is transmitted before a packet or group of packets containing data being transmitted on a low-priority channel. In another implementation, packets containing data being transmitted on a high-priority channel are allocated more transmit slots than packets containing data being transmitted on a low-priority channel. Time-critical messages can be transmitted on the high-priority channel, while relatively unimportant messages can be transmitted on the low-priority channel. The system hardware can automatically transmit a portion of a message once enough data is written into a buffer to fill a packet. That is, message transmission can be performed as data becomes available and need not wait until an entire message is written into the buffer.

The XOFF bits in the third byte 203 control the flow of data in the channels. Each node can include multiple hardware buffers that receive messages transmitted on a respective one of the multiple channels. For example, high-priority messages are stored in a high-priority buffer and low-priority messages are stored in a low-priority buffer. When a first node that transmits the packet 200 sets an XOFF bit in the packet 200, the first node is instructing a second node that receives the packet 200 to stop transmitting data to the first node on the respective data channel. The first node's hardware can automatically set an XOFF bit for a data channel, for example, when a buffer into which the first node places messages from that data channel is becoming full. In one implementation, a threshold for when a node sets the XOFF bit for a given channel is set equal to the size of the respective channel's receive buffer in the node (e.g., 512 words) minus 32 words (4 packets). The 32-word margin gives the receiving node time to receive and act on the XOFF signal with a margin for error. Other threshold levels are possible. The first node's hardware also can set the XOFF bit for the data channel when a large number (e.g., 12) of messages are in the receive buffer. The hardware can automatically clear the XOFF bit for the data channel once packets or messages are removed from the buffer. Each priority channel can have a respective receive buffer in a node. Because the XOFF bits are transmitted in every packet, the error-checking field applies to the XOFF bits and guards against corruption of the XOFF bits.

Multiple channels of communication can be made available in the link layer using the channel-select subfield described above. For example, a hardware channel and high-, medium-, and low-priority channels can be implemented. Messages can vary in length (e.g., between 3 and 128 words) and can be transmitted in one or more packets, depending on the length of the message. The first byte of a message can contain the address of a destination node for the message. System hardware can fragment messages into multiple packets at a transmitting node and defragment the messages at a receiving node. If a message does not fill the data portion of a packet, filler data can be inserted into the remainder of the data portion. Transmit and receive buffers for the messages can be implemented in hardware. For example, a node can include hardware transmit and receive buffers for each channel (e.g., high-, medium-, and low-priority channels). In one implementation, transmit and receive buffers for the channels are 1.5 times a maximum message size.

FIG. 3 shows a conceptual timing diagram for communication between two nodes using packets such as those discussed in the context of FIG. 2. Packets 301-304 are transmitted sequentially from a primary node to a secondary node. Packets 311-314 are received at the secondary node and correspond to the packets 301-304, although the packets 311-314 may be corrupted versions of the respective packets 301-304 if transmission errors occurred. The receipt of the packets 311-314 is delayed in time relative to the transmission of the packets 301-304 because of the finite propagation time of the packet along a link. In the example shown in FIG. 3, the propagation time of the packet is less than the duration of the packet (the amount of time required by the primary node to transmit the packet).

The secondary node transmits packets 355-358 to the primary node. Packets 365-368 are received at the primary node after a delay and correspond to the packets 355-358. The Packet 356 includes an acknowledgement field that applies to the packet 301. If the packet 311 (which corresponds to packet 301) was received correctly at the secondary node, the packet 356 includes an ACK for packet 301. If the packet 311 was not received correctly, the packet 356 includes a NAK. The packet 357 includes an acknowledgement field corresponding to the packet 302. Similarly, the packet 303 includes an acknowledgement field that indicates whether or not the packet 365 was received correctly at the primary node, and the packet 304 includes an acknowledgement field for the packet 366.

In one implementation, the secondary node does not begin transmitting packets until a first acknowledgement field is received from the primary node. For example, the secondary node does not begin transmitting the packet 355 until the secondary node receives the acknowledgement field in the packet 311. To facilitate initial synchronization between the primary and secondary nodes, the two nodes can transmit several sequential synchronization bytes to each other before the primary node transmits the packet 301.

FIG. 3 illustrates a case in which there is a two-packet "pipeline" between the primary and secondary nodes. The packet 356 contains an acknowledgement field for the packet 301. If the acknowledgement field contains an ACK, the primary node transmits the packet 303. If, however, the acknowledgement field of the packet 356 contains a NAK, the primary node can reframe and retransmit the packets 301 and 302. In this implementation, two packets are retransmitted when a NAK is received for the first of the two packets in order to resynchronize the system. If the first of the two packets was not received correctly, the second packet can be retransmitted without checking whether the second packet was received correctly the first time it was transmitted. In a situation where the error in the first packet was caused by loss of synchronization between the two nodes, the second packet would likely contain errors, so the second packet is retransmitted preemptively. The node that transmitted the NAK also will retransmit the last two packets that it transmitted before transmitting the NAK. FIG. 3 is described as having a two-packet pipeline between the primary and secondary nodes because an acknowledgement field is received for a given packet only after another packet has been transmitted. The round-trip time between the primary and secondary nodes is equal to or slightly less than the time required to transmit one packet—that is, the primary node will begin receiving the packet 365 before the primary node has finished transmitting the packet 301. The round-trip time typically depends on the propagation delay over a link and the processing time at a node. Longer round-trip times (longer in absolute time or in time relative to the packet duration) also can be used in a system and can result in a pipeline that is deeper than two packets.

Packets are transmitted substantially continuously between the primary and secondary nodes, regardless of whether there are messages to place in the data fields of the packets. The packets are transmitted in an interlocked manner, as shown in FIG. 3. The interlocked transmission of fixed-length packets causes a fixed phase offset between the packets received at a node and the packets transmitted by the node. The node receives a packet from a remote node that contains an acknowledgement of error-free receipt of a previously transmitted packet a predetermined amount of time after the transmission of the previously transmitted packet. The continuous transmission of interlocked packets allows for high-bandwidth, low-latency communications with precise synchronization between nodes. In addition, the continuous transmission of packets allows the system to calculate the bit error rate (BER) of a connection between nodes accurately and substantially continuously.

As shown in FIG. 4, when the secondary node receives a packet 411 from the primary node and determines that a transmission error occurred that caused the data in the packet 411 to become corrupted, the secondary node finishes transmitting a packet and, instead of transmitting a next packet, transmits a NAK and reframing sequence 456 to the primary node. The reframing sequence 456 is transmitted to reestablish synchronization between the primary and secondary nodes, because one reason that the packet 411 may have been corrupted is that synchronization between the primary and secondary may have been diminished or lost. The reframing sequence can consist of alternating synchronization fields and link fields, where the link field can be a predetermined code such as 0xA3. In one implementation, four link bytes must be received before a node is considered reframed. The primary node receives a NAK and reframing sequence 466 and transmits a reframing sequence 403. After the primary node has transmitted the reframing sequence 403, the primary node resends the last packets that were transmitted before receiving the NAK. In the case of an N-packet pipeline, the last N packets are resent. Once the secondary node receives an ACK in a first retransmitted packet 414, the secondary node also begins retransmitting packets.

As shown in FIG. 5, when the primary node receives a packet 565 from the secondary node and determines that a transmission error occurred that caused the data in the packet 565 to become corrupted, the primary node sends a NAK and reframing sequence 503 to the secondary node. The secondary node receives a NAK and reframing sequence 513 and sends a reframing sequence 557. After the primary node has transmitted the NAK and reframing sequence 503, the primary node resends the last packets that were transmitted before receiving the corrupted packet. Once the secondary node receives an ACK in a first retransmitted packet 514, the secondary node also begins retransmitting packets.

An error counter can keep track of the number of hardware transmission errors that occur in a node. An interrupt can be enabled when the counter reaches a threshold. In one implementation, the error counter can be read by software in the node, and the software can set the interrupt threshold. Error detection and correction can be handled at a very low level in this system, and a software layer operating on top of the described link layer need not implement additional error detection and correction.

FIG. 6 illustrates a process 600 performed at a node in one implementation. The node begins receiving a first packet (step 610) and receives an acknowledgement field in the first packet (step 615). The node determines whether the acknowledgement field is an ACK or a NAK (step 620). If the acknowledgement field is a NAK, the node transmits a reframing sequence (step 625) and retransmits the packet that the received NAK corresponded to along with any packets that were transmitted after that packet (step 630). If the acknowledgement field is an ACK, the node begins transmitting a second packet (step 635) and checks the first packet for errors (step 640), for example, by verifying a CRC value in the packet. If errors were detected in the first packet, the node finishes transmitting the second packet (step 645) and transmits a NAK and reframing sequence (step 650).

If no errors were detected in the first packet, the node determines whether a fault bit was set in the first packet (step 655). If a fault bit was set, the node is put into a fault mode or safe state (step 660). If the fault bit was not set, or once the node is put into a fault mode, the node finishes transmitting the second packet (step 665) and begins transmitting a third packet (step 670).

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, i.e., one or more modules of computer program instructions encoded on a computer-readable medium for execution by, or to control the operation of, data processing apparatus. The computer-readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. For example, the actions recited in the claims can be performed in a different order and still achieve desirable results. The methods, systems, and apparatus described above can be used with various physical transport mechanisms, including fiber optics (e.g., operating at 160 Mb/sec), low-voltage differential signaling (e.g., operating at 122 Mb/sec), source synchronous serial, and asynchronous backplane wires. In one implementation, corrupt packets need not be retransmitted when the packets contain data that can tolerate errors. For example, occasional glitches in a video or audio stream are acceptable. Error detection and reframing can still be used in this implementation to allow fast hardware-implemented recovery from framing errors.

What is claimed is:

1. A method comprising:
   transmitting a first data packet from a first node to a second node, the first data packet including a first data field including non-filler data from the first node;
   receiving the first data packet at the second node, the receipt of the first packet taking a finite amount of time;
   beginning transmission of a second data packet from the second node to the first node after the receipt of the first data packet has begun, but before the receipt of the first data packet has finished;
   receiving the second data packet at the first node, the receipt of the second data packet taking a finite amount of time;
   beginning transmission of a third data packet from the first node to the second node after the transmission of the first data packet has finished, after the receipt of the second data packet has begun, and before the receipt of the second data packet has finished, the transmission of the third data packet beginning before any acknowledgement information corresponding to the first data packet has been received from the second node;
   receiving the third data packet at the second node, the receipt of the third data packet taking a finite amount of time;
   beginning transmission of a fourth data packet from the second node to the first node after the transmission of the second data packet has finished, after the receipt of the third data packet has begun, and before the receipt of the third data packet has finished, the transmission of the fourth data packet beginning before any acknowledgement information corresponding to the second data packet has been received from the first node, the fourth data packet including acknowledgement information indicating whether the first data packet was received correctly by the second node, wherein the transmission of the first data packet and the transmission of the fourth data packet are interlocked such that the fourth data packet is transmitted substantially a predetermined amount of time after the transmission of the first data packet;
   receiving the fourth packet at the first node; and
   processing at the first node the acknowledgement information indicating whether the first data packet was received correctly, the first node retransmitting the first data packet if the first data packet was not received correctly at the second node.

2. The method of claim 1, wherein:
   the second data packet is transmitted regardless of whether the first node has any non-filler data to place in a second data field of the second data packet.

3. The method of claim 1, wherein:
   the first, second, and third data packets each include respective flow-control information, the flow-control information in the first and second data packets relating to the first node, and the flow-control information in the third data packet relating to the second node.

4. The method of claim 3, wherein:
   the flow-control information includes separate flow-control information for multiple channels.

5. The method of claim 1, wherein:
   the first data packet includes header information indicating which of a plurality of channels the non-filler data is being transmitted on.

6. The method of claim 1, wherein:
   the first and second data packets each include an indication of a fault status of the first node; and
   the third data packet includes an indication of a fault status of the second node.

7. The method of claim 1, wherein:
   the first, second, and third data packets have a same length.

8. The method of claim 1, further comprising:
   receiving a fifth data packet at the first node before the third data packet is received, the fifth data packet having been transmitted from the second node before the third data packet, the fifth data packet not including acknowledgement information indicating whether a particular data packet was received correctly by the second node.

9. The method of claim 1, further comprising synchronously communicating data packets between the first node and the second node wherein:
   synchronously communicating includes resending a specific data packet if acknowledgement of receipt of the specific data packet is not received substantially at the predetermined time following transmission of the specific data packet.

10. The method of claim 1, further comprising:
    receiving a packet at the first node, the packet identifying a no acknowledgment (NAK); and
    transmitting a reframing sequence from the first node to the second node to resynchronize the packet flow between the first node and the second node.

11. The method of claim 10, further comprising:
    retransmitting from the first node to the second node a specified number of packets transmitted prior to receipt of the NAK.

12. The method of claim 1, further comprising:
    receiving a packet at the first node from the second node;
    determining at the first node that the received packet has been corrupted; and
    transmitting a no acknowledgement (NAK) and a reframing sequence to the second node, the reframing sequence resynchronizing the packet flow between the first node and the second node.

13. The method of claim 12, further comprising:
    retransmitting from the first node to the second node a specified number of packets transmitted prior to receiving the corrupted packet.

14. The method of claim 1, where each packet has a fixed length such that a fixed phase offset is generated between the packets received at the second node and the packets transmitted by the second node such that packet transmission between the first node and the second node is interlocked.

15. The method of claim 1, further comprising:
continuously transmitting a flow of data packets from the first node to the second node and from the second node to the first node, wherein the flow of data packets includes the first data packet, the second data packet, the third data packet, and the fourth data packet, and wherein data packets of the packet flow are continuously transmitted regardless of whether there are messages to transmit;
wherein if message data is available, then the message data is carried by packets transmitted from the first node to the second node;
wherein if message data is not available, then filler data is carried by packets transmitted from the first node to the second node;
wherein a subsequent packet containing message data is transmitted from the first node to the second node before the first node receives an acknowledgement from the second node that indicates if a previous packet containing message data was correctly received;
wherein the first node receives the acknowledgment at a substantially predetermined time after transmitting the previous data packet; and
wherein if the acknowledgement from the second node indicates the previous packet was not correctly received, then the first node retransmits the message data in the previous data packet to the second node.

16. The method of claim 1, further comprising:
continuously transmitting a flow of data packets from the first node to the second node and from the second node to the first node, wherein the flow of data packets includes the first data packet, the second data packet, the third data packet, and the fourth data packet, and wherein data packets of the packet flow are continuously transmitted regardless of whether there are messages to transmit;
wherein if message data is available, then the message data is carried by packets transmitted from the first node to the second node;
wherein if message data is not available, then filler data is carried by packets transmitted from the first node to the second node;
wherein acknowledgements corresponding to packets transmitted from the first node to the second node are received by the first node from the second node at the same substantially predetermined time interval;
wherein if an acknowledgement corresponding to a particular packet containing message data sent from the first node to the second node is not received at the first node from the second node at the substantially predetermined time, then the first node retransmits the message data in the particular packet to the second node; and
wherein if the acknowledgement corresponding to a particular packet indicates that the packet was not received correctly, then the first node retransmits the message data in the particular packet to the second node.

17. A robotic surgical system comprising:
a first node and a second node, wherein the first node and the second node are configured for communicating data packets between each other, and wherein communicating data packets comprises:
transmitting a first data packet from the first node to the second node, the first data packet including a first data field including non-filler data from the first node;
receiving the first data packet at the second node, the receipt of the first packet taking a finite amount of time;
beginning transmission of a second data packet from the second node to the first node after the receipt of the first data packet has begun, but before the receipt of the first data packet has finished;
receiving the second data packet at the first node, the receipt of the second data packet taking a finite amount of time;
beginning transmission of a third data packet from the first node to the second node after the transmission of the first data packet has finished, after the receipt of the second data packet has begun, and before the receipt of the second data packet has finished, the transmission of the third data packet beginning before any acknowledgement information corresponding to the first data packet has been received from the second node;
receiving the third data packet at the second node, the receipt of the third data packet taking a finite amount of time;
beginning transmission of a fourth data packet from the second node to the first node after the transmission of the second data packet has finished, after the receipt of the third data packet has begun, and before the receipt of the third data packet has finished, the transmission of the fourth data packet beginning before any acknowledgement information corresponding to the second data packet has been received from the first node, the fourth data packet including acknowledgement information indicating whether the first data packet was received correctly by the second node, wherein the transmission of the first data packet and the transmission of the fourth data packet are interlocked such that the fourth data packet is transmitted substantially a predetermined amount of time after the transmission of the first data packet;
receiving the fourth packet at the first node; and
processing at the first node the acknowledgement information indicating whether the first data packet was received correctly, the first node retransmitting the first data packet if the first data packet was not received correctly at the second node.

18. The system of claim 17, wherein:
the second data packet is transmitted regardless of whether the first node has any non-filler data to place in a second data field of the second data packet.

19. The system of claim 17, wherein:
the first, second, and third data packets each include respective flow-control information, the flow-control information in the first and second data packets relating to the first node, and the flow-control information in the third data packet relating to the second node.

20. The system of claim 19, wherein:
the flow-control information includes separate flow-control information for multiple channels.

21. The system of claim 17, wherein:
the first data packet includes header information indicating which of a plurality of channels the non-filler data is being transmitted on.

22. The system of claim 17, wherein:
the first and second data packets each include an indication of a fault status of the first node; and
the third data packet includes an indication of a fault status of the second node.

23. The system of claim 17, wherein:
the first, second, and third data packets have a same length.

24. The system of claim 17, wherein communicating data packets further comprises:
receiving a fifth data packet at the first node before the third data packet is received, the fifth data packet having been transmitted from the second node before the third data packet, the fifth data packet not including acknowledgement information indicating whether a particular data packet was received correctly by the second node.

25. The system of claim 17, wherein communicating data packets further comprises synchronously communicating data packets between the first node and the second node; and
wherein synchronously communicating includes resending a specific data packet if acknowledgement of receipt of the specific data packet is not received substantially at the predetermined time following transmission of the specific data packet.

26. The system of claim 17, wherein communicating data packets further comprises:
receiving a packet at the first node, the packet identifying a no acknowledgment (NAK); and
transmitting a reframing sequence from the first node to the second node to resynchronize the packet flow between the first node and the second node.

27. The system of claim 26, wherein communicating data packets further comprises:
retransmitting from the first node to the second node a specified number of packets transmitted prior to receipt of the NAK.

28. The system of claim 17, wherein communicating data packets further comprises:
receiving a packet at the first node from the second node;
determining at the first node that the received packet has been corrupted;
transmitting a no acknowledgement (NAK) and a reframing sequence to the second node, the reframing sequence resynchronizing the packet flow between the first node and the second node.

29. The system of claim 28, wherein communicating data packets further comprises:
retransmitting from the first node to the second node a specified number of packets transmitted prior to receiving the corrupted packet.

30. The system of claim 17, wherein each packet has a fixed length such that a fixed phase offset is generated between the packets received at the second node and the packets transmitted by the second node such that packet transmission between the first node and the second node is interlocked.

31. The system of claim 17, wherein communicating data packets further comprises:
continuously transmitting a flow of data packets from the first node to the second node and from the second node to the first node, wherein the flow of data packets includes the first data packet, the second data packet, the third data packet, and the fourth data packet, and wherein data packets of the packet flow are continuously transmitted regardless of whether there are messages to transmit;
wherein if message data is available, then the message data is carried by packets transmitted from the first node to the second node;
wherein if message data is not available, then filler data is carried by packets transmitted from the first node to the second node;
wherein a subsequent packet containing message data is transmitted from the first node to the second node before the first node receives an acknowledgement from the second node that indicates if a previous packet containing message data was correctly received;
wherein the first node receives the acknowledgment at a substantially predetermined time after transmitting the previous data packet; and
wherein if the acknowledgement from the second node indicates the previous packet was not correctly received, then the first node retransmits the message data in the previous data packet to the second node.

32. The system of claim 17, wherein communicating data packets further comprises:
continuously transmitting a flow of data packets from the first node to the second node and from the second node to the first node, wherein the flow of data packets includes the first data packet, the second data packet, the third data packet, and the fourth data packet, and wherein data packets of the packet flow are continuously transmitted regardless of whether there are messages to transmit;
wherein if message data is available, then the message data is carried by packets transmitted from the first node to the second node;
wherein if message data is not available, then filler data is carried by packets transmitted from the first node to the second node;
wherein acknowledgements corresponding to packets transmitted from the first node to the second node are received by the first node from the second node at the same substantially predetermined time interval;
wherein if an acknowledgement corresponding to a particular packet containing message data sent from the first node to the second node is not received at the first node from the second node at the substantially predetermined time, then the first node retransmits the message data in the particular packet to the second node; and
wherein if the acknowledgement corresponding to a particular packet indicates that the packet was not received correctly, then the first node retransmits the message data in the particular packet to the second node.

* * * * *